United States Patent [19]

Mehl

[11] Patent Number: 4,922,602

[45] Date of Patent: May 8, 1990

[54] METHOD OF MANUFACTURING A BIOPSY NEEDLE

[75] Inventor: Donald N. Mehl, Minnetonka, Minn.

[73] Assignee: Creative Research and Manufacturing, Inc., Minnetonka, Minn.

[21] Appl. No.: 264,975

[22] Filed: Oct. 31, 1988

Related U.S. Application Data

[63] Continuation of Ser. No. 134,155, Dec. 17, 1987, abandoned, which is a continuation-in-part of Ser. No. 605,809, May 1, 1984, abandoned, which is a continuation of Ser. No. 354,421, Mar. 3, 1982, abandoned, which is a continuation-in-part of Ser. No. 244,015, Mar. 16, 1981, abandoned.

[51] Int. Cl.$^5$ ............................................. B23P 19/04
[52] U.S. Cl. ................................... 29/460; 29/527.4; 81/177.1; 128/753; 264/263; 264/274; 604/264
[58] Field of Search ............................ 29/460, 527.4; 81/177.1; 128/754, 753; 264/263, 274; 604/264

[56] References Cited

U.S. PATENT DOCUMENTS

| | | | |
|---|---|---|---|
| 2,393,751 | 1/1946 | Chotl | 264/274 X |
| 2,985,209 | 5/1961 | Novelo | 81/177.1 |
| 3,173,462 | 3/1965 | Koeppel | 81/177.1 X |
| 3,628,524 | 12/1971 | Jamshidi | 128/754 |
| 3,848,034 | 11/1974 | Schaefer | 264/263 X |
| 3,893,445 | 7/1975 | Hofsess | 128/754 |
| 4,047,278 | 9/1977 | Kurata | 264/263 X |
| 4,258,722 | 3/1981 | Sessions et al. | 128/753 |
| 4,460,159 | 7/1984 | Charlebois et al. | 264/263 X |

Primary Examiner—Charlie T. Moon
Attorney, Agent, or Firm—Hugh D. Jaeger

[57] ABSTRACT

Biopsy needle for bone marrow biopsies or the like including a cannula, a cannula housing supporting the cannula, and a stylet including a stylet cap supporting the stylet wherein the stylet engages into the cannula in a predetermined relationship and the stylet cap interlocks to a cannula housing. The biposy needle is constructed to be either disposable to reusable depending upon the cannula housing and stylet cap material. The end of the cannula is uniquely formed in a swaging, bevel and grinding, and buffing process providing a sharp knife edge. The stylet includes a longitudinal member having a ground and buffed beveled end maintaining a knife-sharp edge around the tip, and the other end of the stylet is bent and molded into the stylet cap where the stylet cap includes a spring detent locking groove for interlocking with the button of the cannula housing. An alternative embodiment discloses a cannula including a tubular cannula member with a preformed sharp end and a clip having outwardly extending flanges at an angle to each other soldered onto an upper portion for securing the cannula tube in the molded cannula housing.

6 Claims, 2 Drawing Sheets

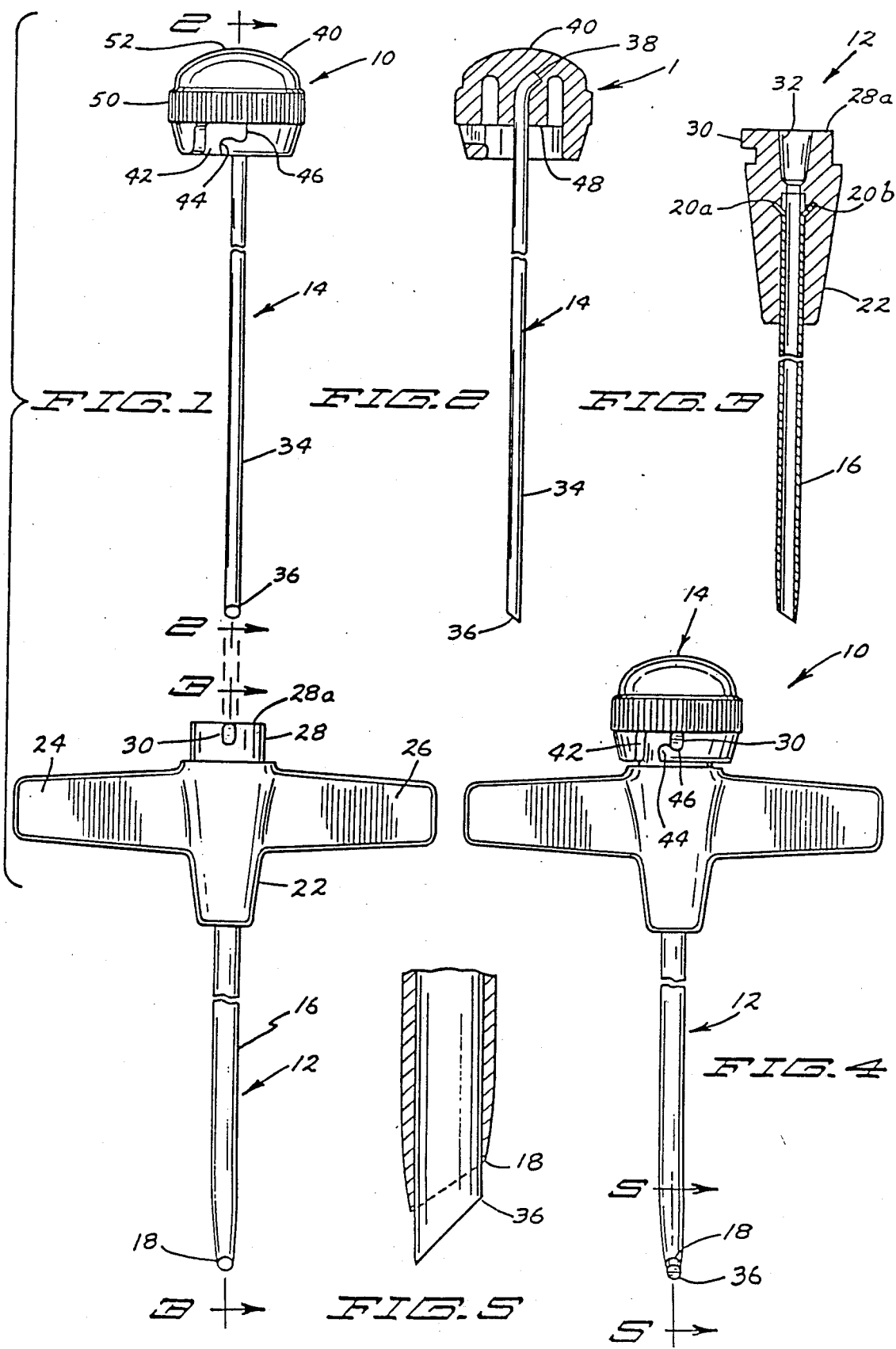

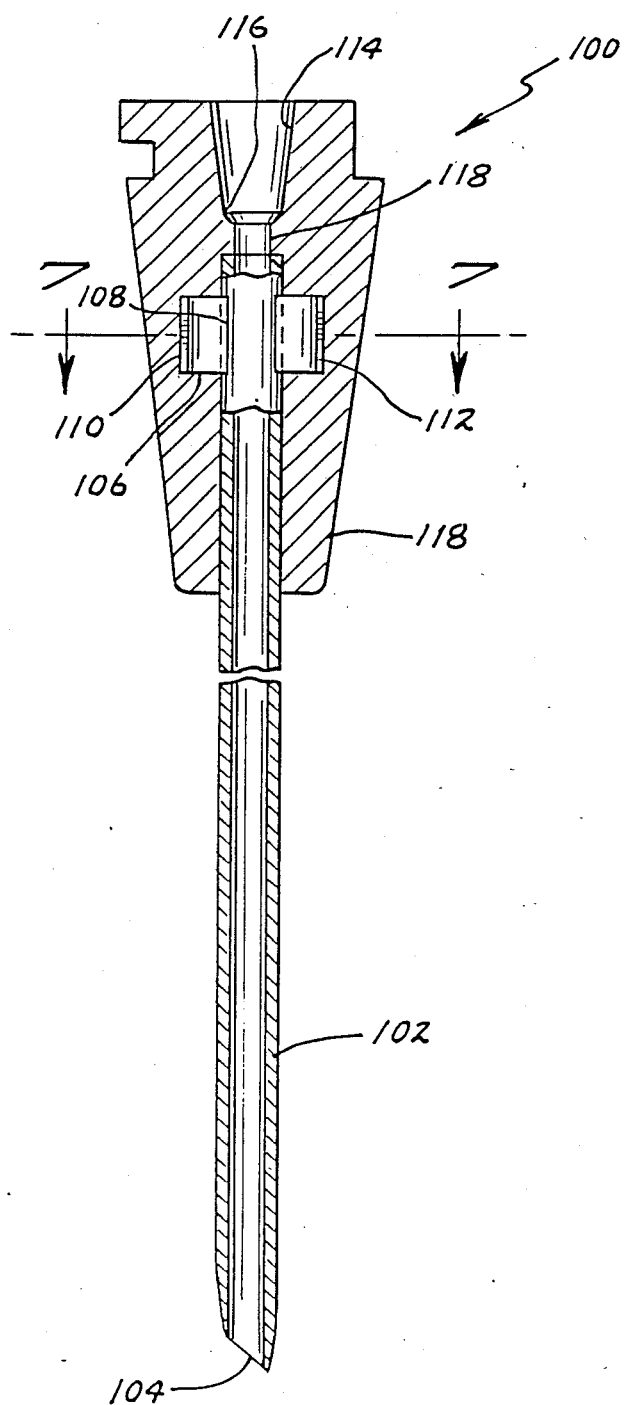

METHOD OF MANUFACTURING A BIOPSY NEEDLE

CROSS REFERENCE TO CO-PENDING APPLICATIONS

This application is a continuation of 07/134,155, filed 12/17/87, now abandoned, which is a continuation of 06/605,809, filed 05/01/84, now abandoned, which is a continuation of 06/354,421, filed 03/03/82, now abandoned, which is a continuation-in-part of 06/244,015, filed 03/16/81, now abandoned.

BACKGROUND OF THE INVENTION

1. Field of the Invention

The present invention pertains to a surgical instrument and, more particularly, pertains to a bone marrow biopsy needle which can be either disposable or reusable. This needle includes a tubular cannula member having a flanged clip which is molded into the housing.

2. Description of the Prior Art

The prior art biopsy needles have all presented some type of drawbacks when used by the physician or surgeon, and which are particularly less than desirable. Some prior art instruments are disposable and cast with very few structural details attended to, with the result that the interlocking between the stylet and the cannula provides for considerable play and the instrument can come apart in the user's hands, resulting in injury not only to the patient but more so to the user by the sharp metal edges poking upwards into the physician's hands. Other prior art devices have some form of interlocking structure but the interlocking structure is not positive, resulting in play between the cannula and stylet during the process of incision into the patient resulting in considerable discomfort. Other types of prior art structures have numerous components which during surgery are not practical in utilization by the user due to the screwing and unscrewing of the fittings.

More importantly, all of the prior art devices have grips which do not really fit into the physician's hand to provide for positive gripping by the physician but have grips which are required to be engaged by the physician in a negative way making the process of biopsy as uncomfortable to the physician/surgeon using the biopsy needle as to the patient. The prior art has failed to recognize that the handles of a biopsy needle must securely engage into the physician's or surgeon's palm for optimum control of the instrument during a biopsy. It is also necessary that the stylet and cannula be engaged to each other during the biopsy process for providing total control to the physician or surgeon.

Prior art needles have secured cannula tubes into the cannula housing in numerous ways providing increased manufacturing processes, resulting in increased end cost to the patient. The prior art has been lacking a needle having a needle readily and cost effectively secured such as though molding into the cannula housing.

The present invention overcomes the disadvantages of the prior art references by providing a biopsy needle having a winged handle and detent locking between the stylet and cannula.

SUMMARY OF THE INVENTION

The general purpose of the present invention is to provide a bone marrow biopsy needle having a cannula and a stylet, both of which engage and interlock with respect to each other, and which can be conveniently grasped by the physician or surgeon in the palm of the hand to provide secure control during the biopsy process.

According to one embodiment of the present invention, there is provided a biopsy needle having a cannula and stylet which interlock with each other, the cannula including a cannula having one end with at least one and preferably two formed members extending outwardly from the end, the other end having a swaged bevel ground and buffed tip providing sharp knife edges in the range of 30–40° with respect to a molded housing, the molding housing molded about the formed members for securing thereto and including two vertically positioned hand wings of decreasing size extending outwardly therefrom, a button extending outwardly from an upward vertical member of reduced diameter with respect to the housing, and an internal bore extending through the housing to the top of the formed end of the cannula for accepting a syringe for drawing of bone marrow during the biopsy, and a stylet including one end having a bend for securing into a stylet cap and the other having a beveled end in the range of 30–60° and buffed to a polished end having a knife-sharp edge about the tip, the stylet cap secured about the bent end of the stylet and having a spring detent locking groove for engaging under and about the button of the cannula in a detented air-locking fashion, and an interior bore of a height to mate with the vertical member of the cannula and engage on the rim of the cannula formed between the housing and the vertical member whereby the stylet is engaged into the cannula housing and detent locking groove in the stylet cap providing for proper engagement between the knife-sharp edges of the cannula and the stylet, thereby providing for proper instrumentation during biopsy.

According to another embodiment of the present invention, there is provided a needle including a molded cannula housing, a tubular cannular member, cylindrical cannula clip having at least one outwardly extending flange and preferably two outwardly extending flanges extending outwardly from the cylindrical axis of the tube and the clip, opposing each other and forming an angle of 45–135° with respect to each other, and soldered to an upper portion of the tubular cannula member whereby the cannula housing is molded about the tubular cannula member and the cannula clip thereby securing the same in the cannula housing.

A significant aspect and feature of the present invention is a biopsy needle having wing-shaped handles facilitating gripping and engagement by the physician or surgeon user.

Another significant aspect and feature of the present invention is an interlocking stylet and cannula providing for not only interlocking of the structural members in a positive detent fashion but also predetermined orientation between the knife sharp edges of the cannula and the stylet. The interlocking structure also positions the stylet at a proper distance from the cannula, providing for consistent and secure biopsy surgery.

An additional significant aspect and feature is a tubular cannular member which is firmly and securely molded in position in the cannular housing through the molded engagement of the cannular clip which is soldered to the tubular cannula member. This protects the surgeon's hand during biopsy as well as the patient.

A further significant aspect and feature of the present invention is a bone marrow biopsy needle which can be constructed either as a disposable instrument or as a reusable instrument depending upon the type of molded material chosen for the cannula and stylet housings.

An additional significant aspect and feature of the present invention is a biopsy needle which can be constructed in different sizes for different sized individuals or for different applications.

Having described one embodiment of the present invention, it is the principal object hereof to provide a bone marrow biopsy needle including a cannula and stylet which interlock with each other. The disclosure also applies to needle structure per se, and is not to be construed as being limited to only biopsy needles, as other applications are inherent within the scope of this disclosure.

BRIEF DESCRIPTION OF THE DRAWINGS

Other objects and many of the attendant advantages of this invention will be readily appreciated as the same becomes better understood by reference to the following detailed description when considered in connection with the accompanying drawings, in which like reference numerals designate like parts throughout the figures thereof and wherein:

FIG. 1 illustrates a perspective view of a cannula and a stylet;

FIG. 2 illustrates a sectional view of the stylet;

FIG. 3 illustrates a sectional view of the cannula;

FIG. 4 illustrates a view of a biopsy needle including the engaged cannula and stylet;

FIG. 5 illustrates an enlarged section of the cannula and stylet knife-sharp edges oriented with respect to each other;

FIG. 6 illustrates a cross-sectional view of an alternative embodiment of the cannular member of the present invention, and;

FIG. 7 illustrates a sectional view taken along line 7—7 of FIG. 6.

DESCRIPTION OF THE PREFERRED EMBODIMENTS

FIG. 1 illustrates a perspective view of a biopsy needle 10 having separated components of a cannula member 12 and a stylet member 14. The cannula member 12 includes a longitudinal cannula 16 having a sharp knife edge 18 which has been swaged, beveled, ground and buffed as later described in detail, formed ends 20a and 20b illustrated in FIG. 2 extending outwardly at an angular tubular relationship, a molded housing 22 of ABS material or the like having the shape as illustrated and having molded thereto left-hand wing 24 and right-hand wing 26, a vertical member 28 extending upwardly, an elongated button 30 extending outwardly, and a chamber 32 running vertically downward from the top of member 28 to the top of the cannula 16 as also illustrated in FIG. 2. The stylet member 14 includes a metal stylet 34 having a sharp edge 36 which has been ground, buffed and polished, a bent end 38 for securing into a molded cap 40, a detent locking groove 42 having a spring member 44 including positive locking member 46. A downward extending boss 48 extends downwardly internal to the cap 40 for engagement with a rim 28a of the cannular housing 22. Locking vertical grooves 50 are provided about the cap for engagement by physician or surgeon user, and a rounded top 52 is provided for an individual's hand.

FIG. 1, which illustrates a cross-sectional view of the cannula member 12, shows the particular detail of the formed ends 20a and 20b securing the cannula 16 into the housing 22 about the vertical chamber 32 which decreases from a large diameter to a small diameter in a lure taper, then to a chamfer, and finally to a diameter which is slightly larger than the internal diameter of the cannular 16 so that a syringe can be inserted into the chamber 32 to draw bone marrow up into the cannula. A probe can be utilized to freely push the bone marrow out through the formed end of the cannula and onto a slide, without damaging or distorting the bone marrow. The detent button 30 and the rim 28a provide for engagement of the stylet member 14 in proper predetermined orientation. The particular detail of the tip 18 of the cannula is also illustrated providing that the angle between the vertical plane and the tip is in the range of 30–45° and preferably 35° plus or minus 5°. The angle between the edge of the cannula and the vertical plane is 13½° plus or minus 1°. This tip structure 18 is obtained through swaging, beveling and grinding, and buffing to provide for a consistent tip for ease of surgery during the biopsy in a process later described in detail.

FIG. 2 illustrates a sectional view of the stylet member 14 where all numerals correspond to those elements previously described. The end of the stylet has an angle between horizontal and the edge of 45° plus or minus 2° while the angle may be in the range of 30–60°. The tip is buffed and polished to maintain a sharp edge. The upper end 38 of the stylet 34 is bent for securing into the cap 40.

MODE OF OPERATION

FIG. 4 illustrates the biopsy needle 10 of the present invention where the stylet member 14 is engaged and interlocked to the cannula member 12. The detent button 30 provides for locking of the members 12 and 14 together by engagement through the groove 42, and up and over the spring member 44 into the positive locking detent 46. A spring member 44 provides a positive sensory digital feedback signal that the members are engaged where button 30 resides in the chamber area of positive locking member 46. The button 30 and positive locking chamber 46 always provide that the knife edges 18 of the cannula 16 and 36 of the stylet 34 are always oriented with respect to each other as illustrated in the figure, and as also illustrated in FIG. 5, providing least minimum effort on the physician's/surgeon's part during the biopsy surgery. The boss 48 of the stylet member 14 seats the stylet onto the cannula at a proper predetermined distance and provides for the orientation of the knife edges. The beveled tips of the stylet and cannula provide for the proper cutting action through the bone due to the wedge action of the tips. The particular angles of the wedges and orientation with respect to each other is one of the keys to obtaining a suitable bone marrow sample during the biopsy process. The contour of the handles 24 and 26 and the winged configuration provide for positive feel to the physician/surgeon during the biopsy. The formed ends 20a and 20b secure the cannula 16 into the housing 22, and maintain round configuration of the cannula tube end 16 in the housing 22, providing for passage of a sample without damaging or distorting the sample.

The end 18 of the cannula 16 is processed according to the predetermined relationship set forth below where:

offset = ½(tan bevel angle)·tan(tip angle)·(I.D.)) and where I.D. is internal diameter of the cannula 16 and offset to a distance between the grinding centerline and the cannula tube centerline.

In process the cannula, first the cannula is formed at the housing end and then swaged over a mandrel to a predetermined internal diameter over a predetermined length from the lower end. Then the cannula is eccentrically rotated about the offset centerline and ground at the same time to achieve the 35° plus or minus 5° tip angle in conjunction with 13½° plus or minus 1° chamfer beveled angle. The beveling of the edge is done at specific orientation to the housing as illustrated in FIG. 2 of the drawing to obtain the predetermined result. After the rotating and grinding operation, the end is buffed and blended to the sharp knife edge for achieving the product by process as illustrated in FIG. 5.

DESCRIPTION OF ALTERNATIVE EMBODIMENT

FIG. 6 illustrates a sectional view of an alternative embodiment of a cannula 100. A tubular cannula member 102 having a preformed end 104 and includes a cannula clip 106 soldered to an upper portion of the member 102 as now described in detail. The cannula clip 106 includes a partial cylindrical member 108 with two outwardly extending wings or 110 and 112 at an angle with respect to each other. The clip 106 has a finite height and is soldered, welded, or the like towards an upper portion of the tubular cannula member 102 as illustrated in FIG. 6.

The gradual taper 114 and lured taper 116 decreases to a constant diameter 118 substantially equal to the inner diameter of the tubular cannula member 102 and mates thereto forming a smooth junction. The cannula housing 118 having a preferred geometrical shape is molded about the tubular cannula member 102 including the clip 106 with flanges 110 and 112 further securing member 102 in engagement to and within the housing 118. The clip 106 soldered or the like to the tube 102 provides for positive and secure engagement to the housing 118. All other structure for engaging to the stylet is identical as previously described for FIGS. 1-5.

FIG. 7 illustrates a sectional view taken along a line 7—7 of FIG. 6 where all numerals correspond to those elements previously described. Attention to drawn to the angle of the wings or flanges 110 and 112 while the cylindrical member 108 is illustrated partially encompassing the tubular cannular member 102. The angle of 110-112 is in the range of 45-135°.

Operation of the cannular 100 of FIGS. 6 and 7 is identical to that of FIGS. 1-5 as previously described.

Various modifications to the biopsy needle of the present invention can be made without departing from the apparent scope thereof. The disclosure is applicable to generic needles and is not to be construed as being limited to biopsy needles. The disclosure is applicable to attachment on a needle to structure in general and for forming a predetermined tip at the end of the needle.

Having thus described the invention, what is claimed is:

1. A method of manufacturing a biopsy cannula having a plastic housing comprising:
   a. forming a clip means having a plurality of outwardly and axially extending wings for reinforcing a cannula tube against rotation of a cannula housing;
   b. fixedly attaching said reinforcing clip means to said cannula tube with said wings extending outwardly and axially of said cannula tube; and
   c. molding said cannula plastic housing about said cannula tube and said wings of said slip to interlock the housing with said clip wings to prevent rotation between said housing and clip.

2. A method according to claim 1 wherein said plurality is two.

3. A method according to claim 2 wherein said two outwardly extending flanges are not coplanar.

4. A method according to claim 3 wherein said attaching further comprises soldering.

5. A method according to claim 3 wherein said attaching further comprises welding.

6. A method according to claim 1 wherein said molding further comprises molding ABS.

* * * * *